United States Patent
Choi et al.

(10) Patent No.: US 8,613,865 B2
(45) Date of Patent: Dec. 24, 2013

(54) AMIDIUM-BASED IONIC LIQUIDS FOR CARBON DIOXIDE ABSORPTION

(75) Inventors: Seok Jin Choi, Gunpo (KR); Jelliarko Palgunadi, Seoul (KR); Je Eun Kang, Seoul (KR); Hoon Sik Kim, Seoul (KR); Sung Yeup Chung, Seoul (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 0 days.

(21) Appl. No.: 13/619,794

(22) Filed: Sep. 14, 2012

(65) Prior Publication Data

US 2013/0012699 A1 Jan. 10, 2013

Related U.S. Application Data

(63) Continuation of application No. 12/570,559, filed on Sep. 30, 2009, now Pat. No. 8,282,710.

(30) Foreign Application Priority Data

Mar. 6, 2009 (KR) .................... 10-2009-0019259

(51) Int. Cl.
*B01D 53/14* (2006.01)

(52) U.S. Cl.
USPC ................. 252/60; 423/228; 252/184; 95/236

(58) Field of Classification Search
None
See application file for complete search history.

(56) References Cited

U.S. PATENT DOCUMENTS

| | | | |
|---|---|---|---|
| 4,990,705 A * | 2/1991 | Nonn | 570/206 |
| 6,579,343 B2 | 6/2003 | Brennecke et al. | |
| 7,220,869 B2 * | 5/2007 | Deng et al. | 548/543 |
| 7,459,011 B2 | 12/2008 | Cadours et al. | |
| 7,459,134 B2 | 12/2008 | Cadours et al. | |
| 7,527,775 B2 | 5/2009 | Chinn et al. | |
| 7,585,479 B2 | 9/2009 | Carrette et al. | |
| 7,670,490 B2 | 3/2010 | Wyse et al. | |
| 2007/0264180 A1 | 11/2007 | Carrette et al. | |
| 2009/0291874 A1 | 11/2009 | Bara et al. | |
| 2010/0319862 A1 | 12/2010 | Rahman | |
| 2011/0129411 A1 * | 6/2011 | Thorn et al. | 423/648.1 |
| 2012/0010334 A1 * | 1/2012 | D'Andola et al. | 524/35 |

FOREIGN PATENT DOCUMENTS

| | | |
|---|---|---|
| JP | 2007-222847 A | 9/2007 |
| JP | 2008-307519 A | 12/2008 |

OTHER PUBLICATIONS

Shiflett et al., "Phase Behavior of Carbon Dioxide in Ionic Liquids: [emim] [Acetate], [emim] [Trifluoroacetate], and [emim] [Acetate] + [emim] [Trifluoroacetate] Mixtures", Journal of Chemical & Engineering Data, vol. 54, No. 1, 108-114 (2009).

Maginn et al., "Desing and Evaluation of Ionic Liquids as Novel CO2 Absorbents", University of Notre Dame, Quarterly Technical Report (2005).

\* cited by examiner

Primary Examiner — Duane Smith
Assistant Examiner — Pankti Patel
(74) Attorney, Agent, or Firm — Edwards Wildman Palmer LLP; Peter F. Corless

(57) ABSTRACT

The present invention relates to a carbon dioxide absorbent, an ionic liquid obtained by reacting amide and an organic acid and a method of using the same. The amidium-based ionic liquid of the present invention has excellent $CO_2$ absorption capability, which is hardly reduced even with repeated use, is easy to synthesize and has low manufacturing cost thus being useful as a $CO_2$ absorbent.

3 Claims, 2 Drawing Sheets

AMIDIUM-BASED IONIC LIQUIDS FOR CARBON DIOXIDE ABSORPTION

CROSS-REFERENCE TO RELATED APPLICATION

This application is a continuation of U.S. application Ser. No. 12/570,559, filed Sep. 30, 2009 which claims the benefit under 35 U.S.C. §119(a) of Korean Patent Application No. 10-2009-0019259 filed on Mar. 6, 2009, the entire contents of which are incorporated herein by reference.

BACKGROUND (a) Technical Field

The present invention relates to a method for using an amidium-based ionic liquid obtained by reacting amide and an organic acid as a carbon dioxide absorbent. More particularly, the present invention relates to a carbon dioxide absorbent, which has excellent carbon dioxide absorption capability, preferably comprising an amidium-based ionic liquid, which is suitably easy to synthesize and has a low manufacturing cost.

(b) Background Art

Methods of separating $CO_2$ from exhaust gases released from large boilers, chemical plants, power plants as well as a natural gas include absorption, adsorption, membrane separation, and cryogenics. In certain cases, when the $CO_2$ concentration being released is low, the method of absorption is preferred. The absorption method is commonly used in industry because it enables the selective separation of certain gases which are well absorbed to an absorbent. However, the absorbent that is used is partially inactivated during the separation and is thus required to be replaced periodically. Preferably, the absorption method employs a liquid absorbent and can be easily replaced, and therefore this method is used in the purification of a large amount of exhaust gases or in gas separation Preferred examples of the carbon dioxide absorbent include aqueous amine-based solutions such as monoethanolamine (MEA), N-methyldiethanolamine (NDEA), diethanolamine (DEA). This is because, when the amine absorbent, which has weak alkalinity, is bound to $CO_2$, which is an acidic gas, and is heat-treated, $CO_2$ can be released and collected while the absorbent is recycled. However, when using this technology, the impurities such as SOx and NOx contained in the absorbed gas tend to decompose amines; heating the absorbent bound to $CO_2$ for breaking the chemical bond between $CO_2$ and the absorbent irreversibly decomposes amines and subsequently deteriorates the capability of the absorbents; the fresh absorbents need to be replenished; amines or their decomposed products cause corrosion of absorption apparatus; high vapor pressure of amines causes the contamination of the $CO_2$ gas released.

To address the above-described properties of the above-mentioned aqueous amine-based absorbents, there have been reports on methods of physically absorbing $CO_2$ by using an organic solvent such as Selexol, IFPexol, NFM, etc.

An important feature of the organic solvent as an absorbent is that $CO_2$ absorption is proceeded via physical interaction between the solvent and $CO_2$, not by the chemical bond as in the case of the aqueous amine-based absorbents, thus requiring a relatively low energy in $CO_2$ recovery and solvent recycling.

In the case of using an amine-based absorbent, $CO_2$ recovery and solvent recycling processes require stripping at high temperature, which is an energy intensive process. However, in the case of physical absorption $CO_2$ can be recovered by means of changing pressure without increasing temperature.

Physical absorption has a low $CO_2$ absorption capability. An organic solvent in general has much lower $CO_2$ absorption capability than aqueous amine-based solution, and thus the circulation rate of an absorbent is high thereby requiring larger equipment.

Physical absorption has a high circulation rate. The physical absorption process by an organic solvent generally requires a circulation rate that is twice as high as that of an aqueous amine-based solution, thus requiring high cost for capital and operation & maintenance.

Physical absorption has a high loss of a solvent. The solvents used in physical absorption have a high vapor pressure and thus can be readily lost during the absorption and regeneration processes. The loss can be suitably minimized by a process of cooling or washing, but to do so requires the installation of additional equipment.

Therefore, there has been an urgent need for the development of a novel absorbent that can replace both amine-based absorbents and organic solvent absorbents, and can resolve the above-mentioned drawbacks of amine-based absorbents and organic solvent absorbents.

As a way to resolve the problems of the conventional absorbents, U.S. Pat. Nos. 6,849,774 and 6,623,659 and published U.S. Pat. Application No. 2008/0146849, incorporated by reference in their entireties herein, disclose attempts made to use ionic liquids, which have no volatility, but with high thermal stability, and maintain liquid state at low temperature of 100 C or below.

An ionic liquid is a salt compound consisting of organic cations and organic or inorganic anions where gas molecules such as CO, $CO_2$, $SO_2$, and $N_2O$ can be well dissolved.

The solubility of a gas to be absorbed into an ionic liquid varies depending on the degree of the mutual interaction between the gas and the ionic liquid. Therefore, the degree of solubility of a gas can be controlled to some extent by adjusting polarity, acidity, alkalinity, and nucleophilicity of an ionic liquid.

Examples of ionic liquids include, but are not limited to, organic cations containing nitrogen such as imidazolium, pyrazolium, triazolium, pyridinium, pyridazinium, pyrimidinium (a quarternary ammonium); halogens such as Cl—, Br—, and I—; and anions such as $BF_4$—, $PF_6$—, $(CF_3SO_2)_2N$—, $CF_3SO_3$—, $MeSO_3$—, $NO_3$—, $CF_3CO_2$—, and $CH_3CO_2$—. In particular, anions containing F atom are known to have relatively high $CO_2$ absorption power.

Ionic liquid absorbents have much lower $CO_2$ absorption capability than the amine-based absorbent. Also, ionic liquid absorbents are detrimental to moisture content thus being readily decomposed by the water contained in a mixed gas, thereby gradually decreasing in absorption power. Ionic liquid absorbents are is not considered economical due to its high manufacturing cost.

The anions containing F atom such as tetrafluoroborate ($BF_4$—), hexafluorophosphate ($PF_6$—), trifluorosulfonimide $[(CF_sSO_2)_2N$—] have high solubility of the acidic gases including $CO_2$ and $CS_2$. However, the manufacturing process of the ionic liquid is rather complex requiring at least 2 steps and also its manufacturing cost is very high thus not suitable for industrial application.

The above information disclosed in this the Background section is only for enhancement of understanding of the background of the invention and therefore it may contain information that does not form the prior art that is already known in this country to a person of ordinary skill in the art.

SUMMARY OF THE DISCLOSURE

In one aspect, the present invention features an amidium-based ionic liquid, which was suitably obtained by reacting amide and carboxylic acid, has high absorption capability for carbon dioxide, has high thermal and chemical stabilities, has low viscosity comparable to an organic solvent, is suitably easy to synthesize and has a suitably low manufacturing cost.

Preferably, an object of the present invention, according to one embodiment, is to provide a carbon dioxide absorbent comprising an amidium-based ionic liquid.

Another object of the present invention, according to further preferred embodiments, is to provide a method for suitably separating carbon dioxide from a mixed gas by using the carbon dioxide absorbent.

In a preferred embodiment, the present invention relates to a carbon dioxide absorbent, which is an ionic liquid, represented by the following formula 1:

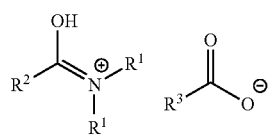

[formula 1]

wherein $R^1$ is $C_1$-$C_8$ alkyl or $C_5$-$C_{15}$ aryl; $R^2$ is $C_1$-$C_6$ alkyl or $C_5$-$C_{15}$ aryl; $R^3$ is $C_1$-$C_6$ alkyl, $C_1$-$C_6$ haloallyl or $C_5$-$C_{15}$ aryl.

The above features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF THE DRAWINGS

The above and other features of the present invention will now be described in detail with reference to certain exemplary embodiments thereof illustrated the accompanying drawings which are given herein below by way of illustration only, and thus are not limitative of the present invention, and wherein.

Figure 1:
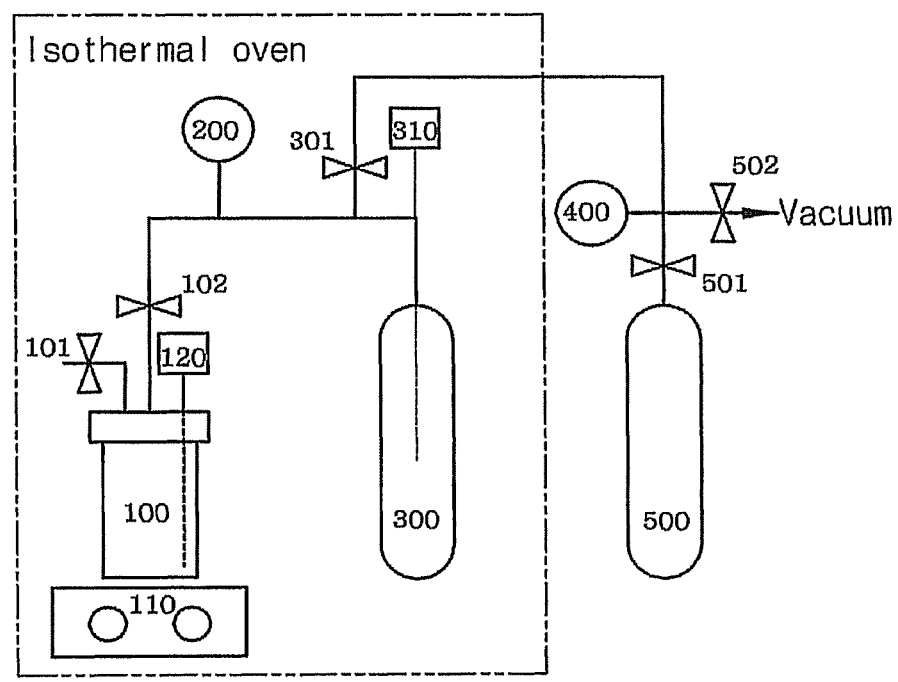
FIG. 1 is a schematic diagram of an apparatus for $CO_2$ absorption experiment.

Reference numerals set forth in the Drawings includes reference to the following elements as further discussed below:

100: $CO_2$ absorption reactor
101: valve
102: valve
110: shaker
120: thermometer
200: high pressure transducer
300: cylinder for $CO_2$ storage
301: valve
310: thermometer
400: pressure gauge
500: container for $CO_2$ supply
501: valve
502: valve It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION OF THE INVENTION

As described herein, the present invention includes a carbon dioxide absorbent, which is an ionic liquid, comprising an amidium-based cation and an anion of an organic acid represented by formula 1:

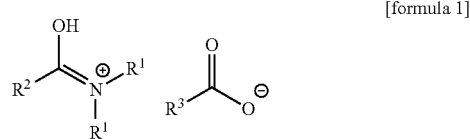

[formula 1]

wherein $R^1$ is $C_1$-$C_8$ alkyl or $C_5$-$C_{15}$ aryl; $R^2$ is $C_1$-$C_6$ alkyl or $C_5$-$C_{15}$ aryl; $R^3$ is $C_1$-$C_6$ alkyl, $C_1$-$C_6$ haloalkyl or $C_5$-$C_{15}$ aryl.

In certain preferred embodiments of the invention, the amidium-based cation is derived from N,N-dimethylformamide, N,N-diethylformamide, N,N-diisopropylformamide, N,N-dibutylformamide, N,N-dimethylacetamide, N,N-diethylacetamide, N,N-dimethylpropionamide, N,N-dimethylbenzamide, N,N-diethylbenzamide, 1-formylpiperidine, caprolactam or N-methylpyrrolidone.

In other preferred embodiments, the anion of an organic acid is derived from acetic acid, trifluoroacetic acid, chloroacetic acid, propionic acid, butanoic acid, hexanoic acid or benzoic acid.

The invention also features, a method of separating carbon dioxide from a gas mixture comprising absorbing carbon dioxide using said carbon dioxide absorbent according to any one of the aspects as described herein.

In one embodiments, the method further comprises stripping said absorbed carbon dioxide from said carbon dioxide absorbent.

In another embodiment, the absorption of carbon dioxide is performed at 0-80 C.

In still another embodiment, the absorption of carbon dioxide is performed under a pressure between atmospheric pressure and 60 atm.

In yet another embodiment, the absorption of carbon dioxide is performed at between room temperature and 100 C.

In still another embodiment, the stripping is performed under a pressure of near zero to atmospheric pressure.

Accordingly, the present invention relates to a carbon dioxide absorbent, which is an ionic liquid, comprising an amidium-based cation and an anion of an organic acid represented by the following formula 1:

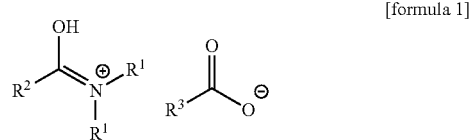

[formula 1]

wherein $R^1$ is $C_1$-$C_8$ alkyl or $C_5$-$C_{15}$ aryl; $R^2$ is $C_1$-$C_6$ alkyl or $C_5$-$C_{15}$ aryl; $R^3$ is $C_1$-$C_6$ alkyl, $C_1$-$C_6$ haloalkyl or $C_5$-$C_{15}$ aryl.

The above alkyl group is preferably a linear or branched hydrocarbon. In particular preferred embodiments, for example the linear or branched hydrocarbon can be, for example, ethyl, methyl, propyl, butyl, pentyl, hexyl, etc., but is not limited to these.

Preferably, the above aryl group includes an aromatic group and its partially reduced derivatives thereof. In further related embodiments, the above aromatic group is a simple or fused cyclic form of a pentagon or a pentadecagon.

In other exemplary embodiments, the representing examples of the aryl group are phenyl, benzyl, naphthyl, imidazolyl, etc., but are not limited to these.

According to certain preferred embodiments of the invention, the above haloalkyl group is meant to refer to an alkyl group where one or more of the hydrogen atom is substituted with a halogen atom, such as trifluoromethyl and chloromethyl, but is not limited to these.

Preferably, the ionic liquid of the present invention represented by the following formula 1 can be suitably prepared by reacting amide represented by the following formula 2 and an organic acid represented by the following formula 3,

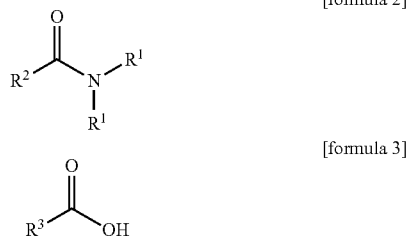

[formula 2]

[formula 3]

wherein $R^1$ is $C_1$-$C_8$ alkyl or $C_5$-$C_{15}$ aryl; $R^2$ is $C_1$-$C_6$ alkyl or $C_5$-$C_{15}$ aryl; and $R^3$ is $C_1$-$C_6$ alkyl, $C_1$-$C_6$ haloalkyl or $C_5$-$C_{15}$ aryl.

Examples of the amide compounds represented by the above formula 2 include, but are not necessarily limited to, N,N-dimethylformamide (DMF), N,N-diethylformamide (DEF), N,N-diisopropylformamide (DIF), N,N-dibutylformamide (DBF), N,N-dimethylacetamide (DMAc), N,N-diethylacetamide (DEAc), N,N-dimethylpropionamide (DMP), N,N-dimethylbenzamide (DMBz), N,N-diethylbenzamide (DEBz), 1-formylpiperidine (1-FP), caprolactam (caprolactam, CAP), and N-methylpyrrolidone (NMP).

Examples of the organic acids represented by the above formula 3 include, but are not necessarily limited to, acetic acid (AA), trifluoroacetic acid (TFA), chloroacetic acid (CA), propionic acid (PA), butanoic acid (BA), hexanoic acid (HA), and benzoic acid (BZA).

According to further preferred embodiments, the carbon dioxide absorbent of the present invention comprises single or a mixture of at least two amide-based ionic liquid. In related embodiments, it has a relatively low viscosity while maintaining a liquid state at room temperature.

In another embodiment, the present invention relates to a method for suitably separating carbon dioxide from a mixed gas by using a carbon dioxide absorbent, comprising:

(1) absorbing carbon dioxide using a carbon dioxide absorbent comprising at least one amide-based ionic liquid represented by the above formula 1, and (2) stripping the absorbed carbon dioxide from the carbon dioxide absorbent.

In further embodiments of the method described herein, the absorption of carbon dioxide in the above step (1) is preferably conducted at between 0-80 C, more preferably at 20 C-50 C, and in still other further embodiments, the method is carried out under a pressure of atmospheric pressure to 60 atm.

Preferably, in carbon dioxide absorption, the amount of carbon dioxide absorption suitably increases as the temperature becomes lower and the higher the pressure. Preferably, the amount of carbon dioxide absorption shows a linear increase in proportion to the increase in pressure.

According to preferred embodiments, the stripping of the absorbed carbon dioxide in the above step (2) is preferably performed at between room temperature and 100 C, more preferably at 40 C-80 C, preferably under a pressure near zero to atmospheric pressure.

The examples of the above mixed gas include the exhaust gas in chemical plants, power plants and large boilers, and a natural gas.

EXAMPLES

The following examples illustrate the invention and are not intended to limit the same.

Preparation Example. Preparation of Amidium-Based Ionic Liquids 0.2 mole of amide was added to a 100 mL flask equipped with a reflux condenser, a dropping funnel and a magnetic rod and then dropwisely added 0.2 mole of an organic acid contained in the dropping funnel thereto while stirring. Upon completion of the reaction, the volatile materials contained in the product from the reaction were suitably removed under vacuum to obtain a transparent hydrophobic amidium-based ionic liquid.

Example 1

$CO_2$ Absorption Capability of DMFH-TFA

DMFH-TFA (N,N-dimethylformamidium trifluoroacetate), an ionic liquid, was prepared by using DMF (N,N-dimethylformamid) and TFA (trifluoroacetatic acid) according to method in the above Preparation Example.

$CO_2$ absorption capability of DMFH-TFA was suitably measured by using an apparatus in FIG. 1. The apparatus depicted in FIG. 1 is similar to the one generally used in physical absorption process, comprising a 60 mL stainless steel absorption reactor (100) equipped with a thermometer (120), a pressure transducer (200) for high pressure (0-1000 psi), a 75 mL cylinder for storage (300) equipped with a thermometer (300), and a shaker (110). This apparatus is suitably installed inside a constant temperature chamber to measure $CO_2$ absorption capability. Outside the constant temperature chamber are a container for $CO_2$ supply (500) and a pressure gauge (400).

To the absorption reactor (100) of FIG. 1 was added 10 g of ionic liquid (N,N-dimethylformamidium trifluoroacetate, DMFH-TFA) synthesized by reaction between DMF and TFA, and $CO_2$ absorption experiment was conducted while maintaining the chamber at 40 C.

After filling a cylinder for $CO_2$ storage (300) with $CO_2$ at certain pressure, a valve (102) was open to expand by an absorption reactor (100) to adjust the initial pressure of the absorption reactor (100) and the whole system at 1 atm, the degree of pressure decrease in the cylinder for $CO_2$ storage (300) was measured until it reached an absorption equilibrium and then the amount of $CO_2$ dissolved in the ionic liquid was suitably calculated by using a gas state equation.

Preferably, in the same manner, the pressure of the whole system was adjusted so that the initial $CO_2$ pressure of the absorption reactor (100) became 5, 10, 15, 20, 30 and 50, respectively, and then the amount of $CO_2$ e absorption according to pressure change was suitably measured. The results are shown in FIG. 2.

Figure 2:
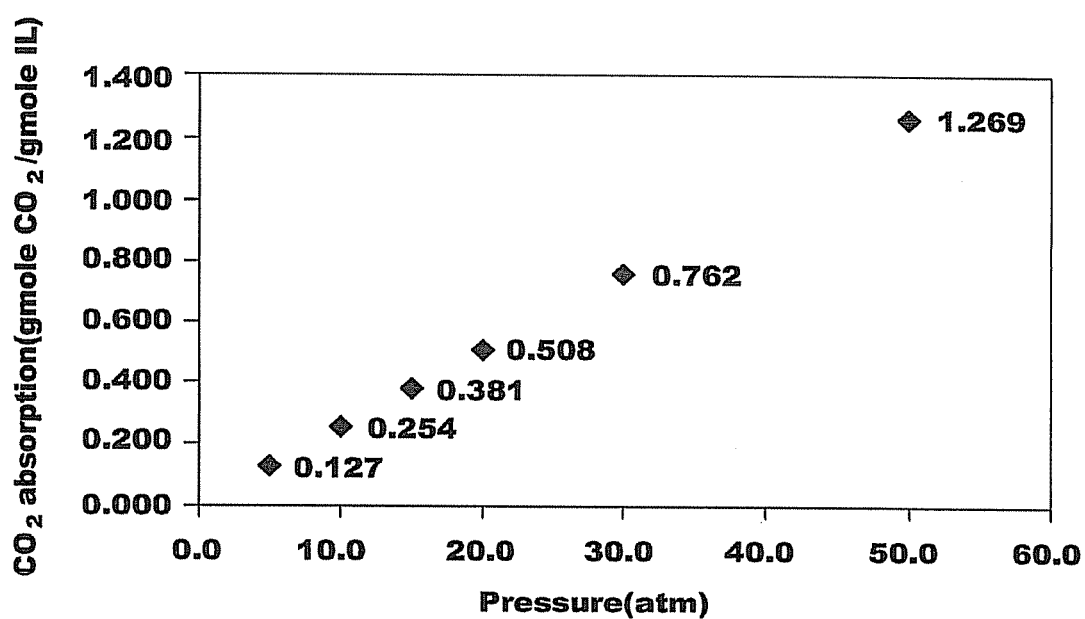
FIG. 2 is a graph showing the amount of $CO_2$ absorbed as increasing pressure in the system.

As shown in FIG. 2, the amount of $CO_2$ absorption of DMFH-TFA rapidly increased in proportion to the increase in the $CO_2$ pressure.

Examples 2-6

$CO_2$ Absorption Capability of DMFH-TFA According to Temperature $CO_2$ absorption experiment was conducted in the same manner as described in Example 1 by using DMFH-IFA as an ionic liquid, fixing absorption pressure at 20 atm, while varying the absorption temperature according to Table 1. The results are also shown in Table 1 below.

TABLE 1

| Example | Ionic liquid | Absorption temperature (° C.) | Amount of $CO_2$ absorption (gmole/IL gmole) |
|---|---|---|---|
| 2 | DMFH-TFA | 20 | 0.695 |
| 3 | DMFH-TFA | 30 | 0.610 |
| 4 | DMFH-TFA | 40 | 0.508 |
| 5 | DMFH-TFA | 50 | 0.424 |
| 6 | DMFH-TFA | 60 | 0.341 |

As shown in the above Table 1, the amount of $CO_2$ absorbed was highest when the absorption temperature was 20 C, and the amount of $CO_2$ that was absorbed decreased as the absorption temperature increased.

Examples 7-12

$CO_2$ Absorption Capability of DMFH as Varying Anion Constituents $CO_2$ absorption experiment was conducted in the same manner as described in Example 1 by using dimethyl formamidium (DMFH) as a cation of an ionic liquid, fixing the absorption temperature at 40 C and absorption pressure at 20 atm, while varying the anions according to Table 2. The results are shown in Table 2 below.

TABLE 2

| Example | Anion | $CO_2$ pressure (atm) | Amount of $CO_2$ absorption (gmole/IL gmole) |
|---|---|---|---|
| 7 | HA | 20 | 0.355 |
| 8 | AA | 20 | 0.363 |
| 9 | BA | 20 | 0.294 |
| 10 | PA | 20 | 0.226 |
| 11 | BZA | 20 | 0.402 |
| 12 | CA | 20 | 0.398 |

As shown in the above Table 2, the amount of $CO_2$ absorption was highest in Example 11 where BZA was used as anion.

Examples 13-26

$CO_2$ Absorption Capability of TFA as Varying Cation Constituents $CO_2$ absorption experiment was conducted in the same manner as shown in Example 1 by fixing the absorption temperature at 30 C, absorption pressure at 20 atm, and using $CF_3CO_2$-(TFA) as anion of the ionic liquid while preferably varying the cation of the ionic liquid according to Table 3 below, thereby measuring equilibration value, and then the pressure was lowered to atmospheric pressure by opening the valve (101) and degassed while varying the temperature as shown in Table 3 below.

After the first absorption and regeneration were completed, the entire process of absorption and degassing were repeated 10 times at the same condition. The initial $CO_2$ absorption capability and the $10^{th}$ $CO_2$ absorption capability were compared and the results are shown in Table 3 below.

TABLE 3

| | | | Amount of $CO_2$ absorption (gmole/IL gmole) | |
|---|---|---|---|---|
| Example | Cation | Regeneration temp. (° C.) | One Absorption | Ten Absorption |
| 14 | DMFH | 70 | 0.610 | 0.604 |
| 15 | DEFH | 70 | 0.637 | 0.630 |
| 16 | DIFH | 70 | 0.662 | 0.655 |
| 17 | DBFH | 70 | 0.674 | 0.668 |
| 18 | DMAcH | 70 | 0.602 | 0.595 |
| 19 | DEAcH | 70 | 0.631 | 0.624 |
| 20 | DMPH | 70 | 0.709 | 0.702 |
| 21 | DMBzH | 70 | 0.757 | 0.751 |
| 22 | DEBzH | 70 | 0.806 | 0.800 |
| 23 | 1-FPH | 70 | 0.734 | 0.729 |
| 24 | CAPH | 70 | 0.782 | 0.775 |
| 25 | NMPH | 70 | 0.593 | 0.588 |
| 26 | DMFH | 80 | 0.609 | 0.604 |
| 27 | DMFH | 40 | 0.610 | 0.597 |

According to the above Table 3, the initial $CO_2$ absorption capability and the $10^{th}$ $CO_2$ absorption capability were highest in Example 21 where the anion used is DEBzH, respectively.

Examples 27-30

$CO_2$ Absorption Capability of Ionic Liquids as Varying Ionic Liquid Constituents $CO_2$ absorption experiment was conducted in the same manner as in Example 1 by fixing the absorption temperature at 30 C, absorption pressure at 20 atm, and using two kinds of ionic liquids as shown in Table 4 below. The results are shown in Table 4 below.

TABLE 4

| Example | Ionic liquid | Amount of $CO_2$ absorption (gmole/IL gmole) |
|---|---|---|
| 27 | DMFH-BZA + DEFH-AA | 0.408 |
| 28 | DMFH-PA + NMPH-BZA | 0.367 |
| 29 | DMFH-BZA + DEAcH-AA | 0.374 |
| 30 | DEFH-PA + DMFH-BZA | 0.492 |

According to the above Table 4, the amount of $CO_2$ absorption was highest in Example 30 where a mixture of DEFH-P and DMFH-BZA was used as an ionic liquid.

Comparative Example

CO₂ Absorption Capability of Diethanolamine

Experiment of absorbing $CO_2$ at 1 atm, 30 C by preferably using diethanolamine (diethanolamine) instead of an ionic liquid as an absorbent and regeneration of the absorbent at atmospheric pressure, 110 C was conducted similarly as described in Example 13. After the first absorption and regeneration were completed, the entire process of absorption and regeneration were repeated at the same condition.

$CO_2$ was absorbed in the amount of 0.1769 gmole/gmole to a solvent in the first absorption, and 0.1440 gmol/gmole in the second absorption, indicating that the $CO_2$ absorption capability was reduced by about 19%.

Therefore, it was confirmed that the $CO_2$ absorption capability of the solvent was considerably reduced when compared to those in the Examples.

Also, the results described herein demonstrate that an ionic liquid is more efficient than an organic solvent absorbent because the ionic liquid has better $CO_2$ absorption capability than the organic solvent absorbent thus enabling circulation rate and reducing the size of an apparatus.

INDUSTRIAL APPLICABILITY

As described herein, the amidium-based ionic liquid of the present invention requires a much lower energy for the process of stripping of absorbed $CO_2$ than that of conventional amine-based absorbent requiring suitably high temperature for $CO_2$ collection. This is because $CO_2$ can be more easily removed from an ionic liquid, where $CO_2$ is absorbed by means of physical interaction, than from an amine-based solution, which forms a chemical bond with $CO_2$.

Further, an ionic liquid is also more efficient than an organic solvent absorbent because the ionic liquid has better $CO_2$ absorption capability than the organic solvent absorbent thus enabling circulation rate and suitably reducing the size of an apparatus.

Further, the ionic liquid has a much lower hydrocarbon absorption rate than the organic solvent absorbent, and thus it can minimize the loss of hydrocarbons by selectively absorbing only $CO_2$ during the purification of hydrocarbons such as a natural gas which contains $CO_2$ impurities.

According to the present invention, the ionic liquid absorbent has almost no loss. The ionic liquid absorbent used in the present invention has a very low vapor pressure and thus it can hardly undergo a loss, and the loss via decomposition is very low because it is chemically and thermally stable.

Further, the amidium-based ionic liquid of the present invention has the advantages of superior $CO_2$ absorption capability, can easily strip $CO_2$, and maintain the level of absorption capability almost equal to that at the beginning even after repeated use.

While the present invention has been shown and described with reference to certain exemplary embodiments thereof, it will be understood by those skilled in the art that various changes in form and details may be made therein without departing from the spirit and scope of the present invention as defined by the appended claims and their equivalents.

The invention claimed is:

1. A carbon dioxide absorbent, which is an ionic liquid, comprising an amidium-based cation and an anion of an organic acid represented by the following formula 1:

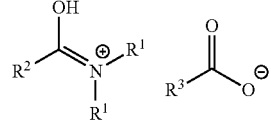

[formula 1]

wherein $R^1$ is $C_1$-$C_8$ alkyl or $C_5$-$C_{15}$ aryl; $R^2$ is $C_1$-$C_6$ alkyl or $C_5$-$C_{15}$ aryl; $R^3$ is $C_1$-$C_6$ alkyl, $C_1$-$C_6$ haloalkyl or $C_5$-$C_{15}$ aryl.

2. The carbon dioxide absorbent according to claim 1, wherein said amidium-based cation is derived from N,N-dimethylformamide, N,N-diethylformamide, N,N-diisopropylformamide, N,N-dibutylformamide, N,N-dimethylacetamide, N,N-diethylacetamide, N,N-dimethylpropionamide, N,N-dimethylbenzamide, N,N-diethylbenzamide, 1-formylpiperidine, caprolactam or N-methylpyrrolidone.

3. The carbon dioxide absorbent according to claim 1, wherein said anion of an organic acid is derived from acetic acid, trifluoroacetic acid, chloroacetic acid, propionic acid, butanoic acid, hexanoic acid or benzoic acid.

* * * * *